United States Patent
Ling et al.

(10) Patent No.: US 10,936,846 B2
(45) Date of Patent: Mar. 2, 2021

(54) OPTICAL FINGERPRINT SENSOR APPARATUS AND ASSEMBLING METHOD THEREOF

(71) Applicant: SHANGHAI OXI TECHNOLOGY CO., LTD, Shanghai (CN)

(72) Inventors: Yan Ling, Shanghai (CN); Hong Zhu, Shanghai (CN)

(73) Assignee: SHANGHAI OXI TECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 16/761,083

(22) PCT Filed: Aug. 17, 2018

(86) PCT No.: PCT/CN2018/100984
§ 371 (c)(1),
(2) Date: May 1, 2020

(87) PCT Pub. No.: WO2020/034184
PCT Pub. Date: Feb. 20, 2020

(65) Prior Publication Data
US 2020/0401779 A1    Dec. 24, 2020

(51) Int. Cl.
*G06K 9/00*    (2006.01)
(52) U.S. Cl.
CPC .................. *G06K 9/0004* (2013.01)
(58) Field of Classification Search
CPC .................................................. G06K 9/0004
See application file for complete search history.

(56) References Cited

U.S. PATENT DOCUMENTS 10,409,099 B2 *  9/2019  Hsiao ................... G02F 1/13338
10,699,094 B2 *  6/2020  Shim ................... G06K 9/00013
(Continued)

FOREIGN PATENT DOCUMENTS

CN          107358139 A       11/2017
CN          207148869 (U)      3/2018

OTHER PUBLICATIONS

International Search Report from PCT/CN2018/100984 dated Aug. 17, 2018.

*Primary Examiner* — Utpal D Shah
(74) *Attorney, Agent, or Firm* — Adsero IP

(57) ABSTRACT

An optical fingerprint sensor apparatus and an assembling method thereof are provided. The optical fingerprint sensor apparatus includes: a support frame structure having an opening therein, the opening penetrating through the support frame structure; an optical fingerprint sensor module disposed in the opening; a support plate disposed below the optical fingerprint sensor module and at the bottom of the support frame structure, wherein the support plate is fixedly connected to the bottom of the support frame structure; an elastic support member disposed between the optical fingerprint sensor module and the support plate, wherein the elastic support member is fixedly connected to the optical fingerprint sensor module and the support plate, respectively; and a self-luminous display panel disposed on the optical fingerprint sensor module and the support frame structure, wherein the self-luminous display panel and the support frame structure are fixedly connected. Performance of the optical fingerprint sensor apparatus is improved.

20 Claims, 6 Drawing Sheets

(56) References Cited

U.S. PATENT DOCUMENTS

| | | | |
|---|---|---|---|
| 2017/0091515 A1* | 3/2017 | Cao | G06F 1/1637 |
| 2018/0082102 A1* | 3/2018 | Lee | G06K 9/00912 |
| 2018/0121703 A1* | 5/2018 | Jung | G06K 9/0004 |
| 2018/0151641 A1* | 5/2018 | Choo | G06F 1/1643 |
| 2018/0218194 A1* | 8/2018 | Lee | H04N 1/00307 |
| 2018/0330141 A1* | 11/2018 | Yang | G06F 1/1684 |
| 2018/0365466 A1* | 12/2018 | Shim | G06K 9/00087 |
| 2019/0116314 A1* | 4/2019 | Tran | H04N 13/194 |
| 2020/0311368 A1* | 10/2020 | Koda | G06T 1/00 |

* cited by examiner

OPTICAL FINGERPRINT SENSOR APPARATUS AND ASSEMBLING METHOD THEREOF

CROSS-REFERENCE TO RELATED APPLICATIONS

This application is a 35 U.S.C. § 371 national phase application of PCT/CN2018/100984, filed on Aug. 17, 2018, entitled "Optical Fingerprint Sensor Apparatus and Assembling Method Thereof", which is incorporated herein by reference in its entirety.

TECHNICAL FIELD

The present disclosure relates to an optical fingerprint recognition field, and more particularly relates to an optical fingerprint sensor apparatus and an assembling method thereof.

BACKGROUND

Fingerprint imaging recognition technology is used to realize identification by capturing fingerprint images of persons using optical fingerprint sensors and then determining whether the fingerprint images match those already stored in a system. Due to its convenience in use and uniqueness of human fingerprints, the fingerprint recognition technology has been widely applied to various fields, such as safety inspection field (for example, public security bureau or customs), entrance guard systems in buildings, consumption goods field (for example, personal computers or mobile phones), and the like.

The fingerprint recognition technology includes optical imaging, capacitive imaging, ultrasonic imaging and the like, among which, the optical fingerprint recognition technology is advantageous in imaging quality and cost.

However, performance of existing optical fingerprint sensor apparatuses needs to be improved.

SUMMARY

In embodiments of the present disclosure, an optical fingerprint sensor apparatus and an assembling method thereof are provided to improve performance of the optical fingerprint sensor apparatus.

In an embodiment of the present disclosure, an optical fingerprint sensor apparatus is provided, including: a support frame structure having an opening therein, the opening penetrating through the support frame structure; an optical fingerprint sensor module disposed in the opening; a support plate disposed below the optical fingerprint sensor module and at the bottom of the support frame structure, wherein the support plate is fixedly connected to the bottom of the support frame structure; an elastic support member disposed between the optical fingerprint sensor module and the support plate, wherein the elastic support member is fixedly connected to the optical fingerprint sensor module and the support plate, respectively; and a self-luminous display panel disposed on the optical fingerprint sensor module and the support frame structure, wherein the self-luminous display panel and the support frame structure are fixedly connected.

Optionally, the optical fingerprint sensor module is in contact with and separable from the self-luminous display panel.

Optionally, the optical fingerprint sensor module includes a frame region, and the optical fingerprint sensor apparatus further includes a buffer layer disposed between the frame region of the optical fingerprint sensor module and the self-luminous display panel, wherein the buffer layer is adhered to the frame region of the optical fingerprint sensor module, and is in contact with and separable from the self-luminous display panel.

Optionally, the buffer layer includes organic polymer.

Optionally, elastic modulus of the buffer layer is within a range from 100 MPa to 10000 MPa.

Optionally, thickness of the buffer layer in a compressed state is within a range from 0.05 mm to 1 mm, and a size of a gap between the self-luminous display panel and the optical fingerprint sensor module is within a range from 0.05 mm to 1 mm.

Optionally, the elastic support member is a spring, wherein the spring has a first connection terminal and a second connection terminal opposite to each other in a compression direction of the spring, the first connection terminal is fixedly connected to the bottom of the optical fingerprint sensor module, and the second connection terminal is fixedly connected to the support plate.

Optionally, the elastic support member is an elastic foam.

Optionally, elastic modulus of the elastic foam is within a range from 10 MPa to 10000 MPa.

Optionally, the elastic support member is an elastic slice or a damper.

Optionally, the optical fingerprint sensor apparatus further includes a fastener penetrating through the support plate and a portion of the support frame structure.

Optionally, the optical fingerprint sensor module includes an optical fingerprint sensor and a collimator disposed on the optical fingerprint sensor, wherein the collimator is adhered to the optical fingerprint sensor, and is disposed between the optical fingerprint sensor and the self-luminous display panel.

Optionally, the optical fingerprint sensor apparatus further includes a cover layer on the self-luminous display panel.

In an embodiment of the present disclosure, a method for assembling an optical fingerprint sensor apparatus is provided, including: providing an optical fingerprint sensor module, a self-luminous display panel, a support plate, an elastic support member and a support frame structure, wherein the support frame structure has an opening therein which penetrates through the support frame structure; disposing the elastic support member between the optical fingerprint sensor module and the support plate, and fixedly connecting the elastic support member to the optical fingerprint sensor module and the support plate, respectively; fixedly connecting the self-luminous display panel to the support frame structure, wherein the self-luminous display panel faces the opening; following fixedly connecting the elastic support member to the optical fingerprint sensor module and the support plate, respectively and fixedly connecting the self-luminous display panel to the support frame structure, disposing the optical fingerprint sensor module in the opening, to make the optical fingerprint sensor module disposed between the self-luminous display panel and the support plate, wherein the support plate faces the support frame structure; and following disposing the optical fingerprint sensor module in the opening, compressing the elastic support member, and fixedly connecting the support plate to the support frame structure.

Optionally, the optical fingerprint sensor module is disposed in the opening, to make the optical fingerprint sensor module contact with the self-luminous display panel, and the elastic support member is compressed and the support plate is fixedly connected to the support frame structure, to make the optical fingerprint sensor module and the self-luminous display panel squeeze each other.

Optionally, the optical fingerprint sensor module includes a frame region, and the method further includes: providing a buffer layer; prior to disposing the optical fingerprint sensor module in the opening, adhering the buffer layer to a surface of the frame region of the optical fingerprint sensor module; following fixedly connecting the elastic support member to the optical fingerprint sensor module and the support plate, respectively, the buffer layer and the elastic support member being disposed on two sides of the optical fingerprint sensor module; during disposing the optical fingerprint sensor module in the opening, disposing the buffer layer in the opening, wherein the buffer layer is in contact with the self-luminous display panel; and during compressing the elastic support member, compressing the buffer layer.

Optionally, the buffer layer includes organic polymer, and elastic modulus of the buffer layer is within a range from 100 MPa to 10000 MPa.

Optionally, thickness of the buffer layer in a compressed state is within a range from 0.05 mm to 1 mm, and a size of a gap between the self-luminous display panel and the optical fingerprint sensor module is within a range from 0.05 mm to 1 mm.

Optionally, the support plate is fixedly connected to the support frame structure with a fastener.

Optionally, the method further includes: providing a cover layer; prior to fixedly connecting the self-luminous display panel to the support frame structure, adhering the self-luminous display panel to the cover layer, wherein after the self-luminous display panel is fixedly connected to the support frame structure, the cover layer and the support frame structure are disposed on two sides of the self-luminous display panel.

Embodiments of the present disclosure may provide following advantages. In the optical fingerprint sensor apparatus provided in embodiments of the present disclosure, a support frame structure is provided between the self-luminous display panel and the support plate, and both the self-luminous display panel and the support plate are fixedly connected to the support frame structure. An optical fingerprint sensor module is disposed within the support frame structure, and an elastic support member is provided between the optical fingerprint sensor module and the support plate. The support plate, the elastic support member and the support frame structure together limit a relative position of the self-luminous display panel and the optical fingerprint sensor module, to make positions of the optical fingerprint sensor module and the self-luminous display panel relatively fixed. Accordingly, there is no need to stick the optical fingerprint sensor module to the self-luminous display panel. When a fixing force between the support frame structure and the support plate is released, the elastic support member can restore to a non-compressed state, so that the optical fingerprint sensor module is separated from the self-luminous display panel. In this way, when the optical fingerprint sensor module or the self-luminous display panel is damaged, the optical fingerprint sensor module can be reassembled between the self-luminous display panel and the elastic support member without discarding the self-luminous display panel or the optical fingerprint sensor module, which allows the self-luminous display panel or the optical fingerprint sensor module to be reused. Therefore, performance of the optical fingerprint sensor apparatus is improved.

DETAILED DESCRIPTION

As described in the background, performance of existing optical fingerprint sensor apparatuses needs to be improved.

Figure 1:
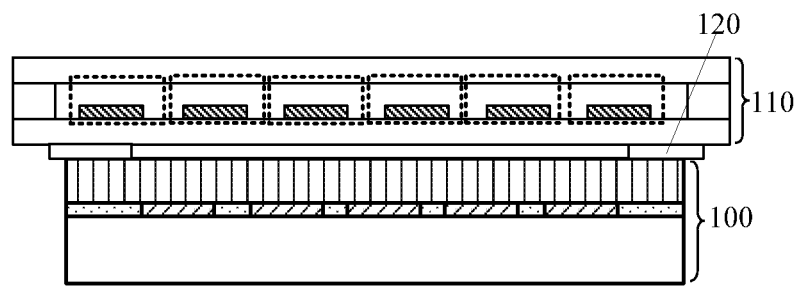
FIG. 1 schematically illustrates a structural diagram of an optical fingerprint sensor apparatus in existing techniques.

FIG. 1 schematically illustrates a structural diagram of an optical fingerprint sensor apparatus in existing techniques. Referring to FIG. 1, the optical fingerprint sensor apparatus includes: an optical fingerprint sensor module 100 which includes an active region and a frame region disposed around the active region; a self-luminous display panel 110 disposed on the optical fingerprint sensor module 100; and a frame-shaped double-sided adhesive layer 120 disposed between the frame region of the optical fingerprint sensor module 100 and the self-luminous display panel 110.

The optical fingerprint sensor module 100 is adhered to the self-luminous display panel 110 through the frame-shaped double-sided adhesive layer 120.

As the frame-shaped double-sided adhesive layer 120 is employed to adhere the frame region of the optical fingerprint sensor module 100 to the self-luminous display panel 110, it is prone to remove the optical fingerprint sensor module 100 from one side of the double-sided adhesive layer 120 when the optical fingerprint sensor module 100 is damaged. However, when the optical fingerprint sensor module 100 or the self-luminous display panel 110 is damaged, if the optical fingerprint sensor module 100 is removed from one side of the double-sided adhesive layer 120, there is still a risk that the optical fingerprint sensor module 100 or the self-luminous display panel 110 will be damaged. As a result, a reuse rate of the optical fingerprint sensor module 100 and the self-luminous display panel 110 is relatively low.

Therefore, embodiments of the present disclosure provide an optical fingerprint sensor apparatus, including: a support frame structure having an opening therein, the opening penetrating through the support frame structure; an optical fingerprint sensor module disposed in the opening; a support plate disposed below the optical fingerprint sensor module and at the bottom of the support frame structure, wherein the support plate is fixedly connected to the bottom of the support frame structure; an elastic support member disposed between the optical fingerprint sensor module and the support plate, wherein the elastic support member is fixedly connected to the optical fingerprint sensor module and the support plate, respectively; and a self-luminous display panel disposed on the optical fingerprint sensor module and the support frame structure, wherein the self-luminous display panel and the support frame structure are fixedly connected. Performance of the optical fingerprint sensor apparatus is improved.

In order to clarify the object, characteristic and advantages of embodiments of the present disclosure, embodiments of present disclosure will be described clearly in detail in conjunction with accompanying drawings.

The up-down relationship in the disclosure is defined by placing the optical fingerprint sensor apparatus under a user's eyes. When the optical fingerprint sensor apparatus is placed under the eyes of the user and a display surface of the self-luminous display panel faces up, if a first structure is disposed above a second structure, it means that the first structure is closer to the user's eyes than the second structure.

FIGS. 2 to 10 schematically illustrate structural diagrams of an optical fingerprint sensor apparatus during its assembling process according to an embodiment.

Figure 2:
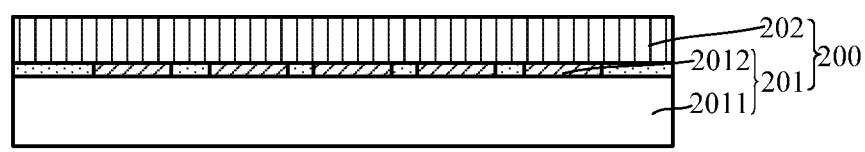
FIGS. 2 to 10 schematically illustrate structural diagrams of an optical fingerprint sensor apparatus during its assembling process according to an embodiment.

Referring to FIG. 2, an optical fingerprint sensor module 200 is provided.

In some embodiments, the optical fingerprint sensor module 200 includes an optical fingerprint sensor 201 and a collimator 202. The collimator 202 is disposed on the optical fingerprint sensor 201, and is adhered to the optical fingerprint sensor 201.

The optical fingerprint sensor 201 includes a sensor non-opaque substrate 2011 (refer to FIG. 2) and a fingerprint sensing circuit layer 2012 (refer to FIG. 2) disposed on a surface of the sensor non-opaque substrate 2011. The sensor non-opaque substrate 2011 may include a glass plate or a plastic plate, and the plastic substrate may include a Polyimide (PI) substrate or a Polyethylene terephthalate (PET) substrate.

The fingerprint sensing circuit layer 2012 includes a plurality of columns of signal lines, a plurality of rows of first driving lines, and a photosensitive pixel array. The photosensitive pixel array includes a plurality of photosensitive pixel cells each of which includes a photosensitive member and a switching member. The photosensitive member includes a photodiode. The plurality of rows of first driving lines are used to turn on the photosensitive pixel cells row by row.

The collimator 202 and the sensor non-opaque substrate 2011 are disposed on two sides of the fingerprint sensing circuit layer 2012, respectively.

The collimator 202 is subsequently disposed between the optical fingerprint sensor 201 and a self-luminous display panel. The collimator 202 only allows light at a certain angle to pass through the self-luminous display panel, thereby eliminating stray light.

In some embodiments, the optical fingerprint sensor module may be an optical fingerprint sensor manufactured based on a Complementary Metal-Oxide-Semiconductor Transistor (CMOS) process using a single crystal silicon as a substrate.

Figure 3:
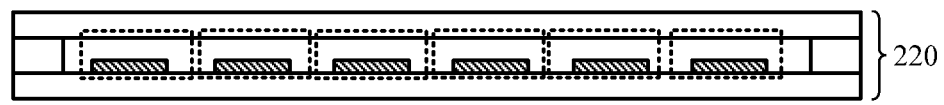

Referring to FIG. 3, a self-luminous display panel 220 is provided.

The self-luminous display panel 220 includes a first non-opaque substrate, a second non-opaque substrate, and a self-luminous circuit layer disposed between the first non-opaque substrate and the second non-opaque substrate. A material of the first non-opaque substrate and the second non-opaque substrate may be a non-opaque material, such as inorganic glass or organic glass, or plastic products other than organic glass, for example, a plastic substrate. The plastic substrate includes a PI substrate or a PET substrate.

The self-luminous circuit layer includes a self-luminous display array, a plurality of rows of second driving lines, and a plurality of columns of data lines. The self-luminous display array includes a plurality of self-luminous display cells.

In some embodiments, the self-luminous display panel 220 is an Organic Light Emitting Diode (OLED) display panel.

Figure 4:
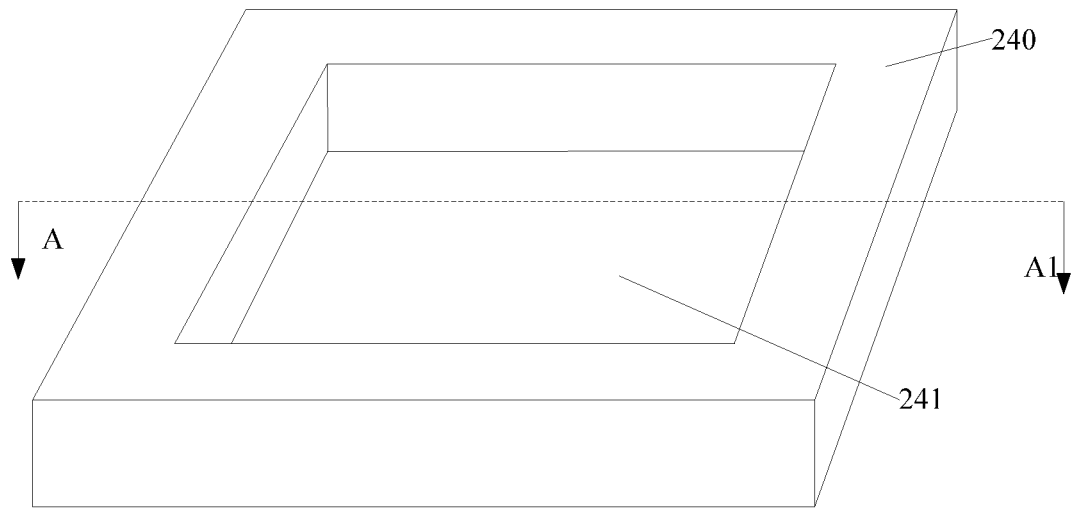
Figure 5:

Referring to FIGS. 4 and 5, FIG. 4 is a schematic perspective view of a support frame structure, and FIG. 5 is a cross-sectional view along a cutting line A-A1 in FIG. 4. A support frame structure 240 is provided with an opening 241 therein. The opening 241 penetrates through the support frame structure 240.

The support frame structure 240 has a first frame connection surface 2411 and a second frame connection surface 2412 opposite to each other. The opening 241 penetrates through the support frame structure 240 in a direction from the first frame connection surface 2411 to the second frame connection surface 2412.

In some embodiments, the support frame structure 240 has a rectangular ring structure, and an edge of the opening 241 is rectangular. In other embodiments, the support frame structure may have other shapes, which is not limited.

Figure 6:
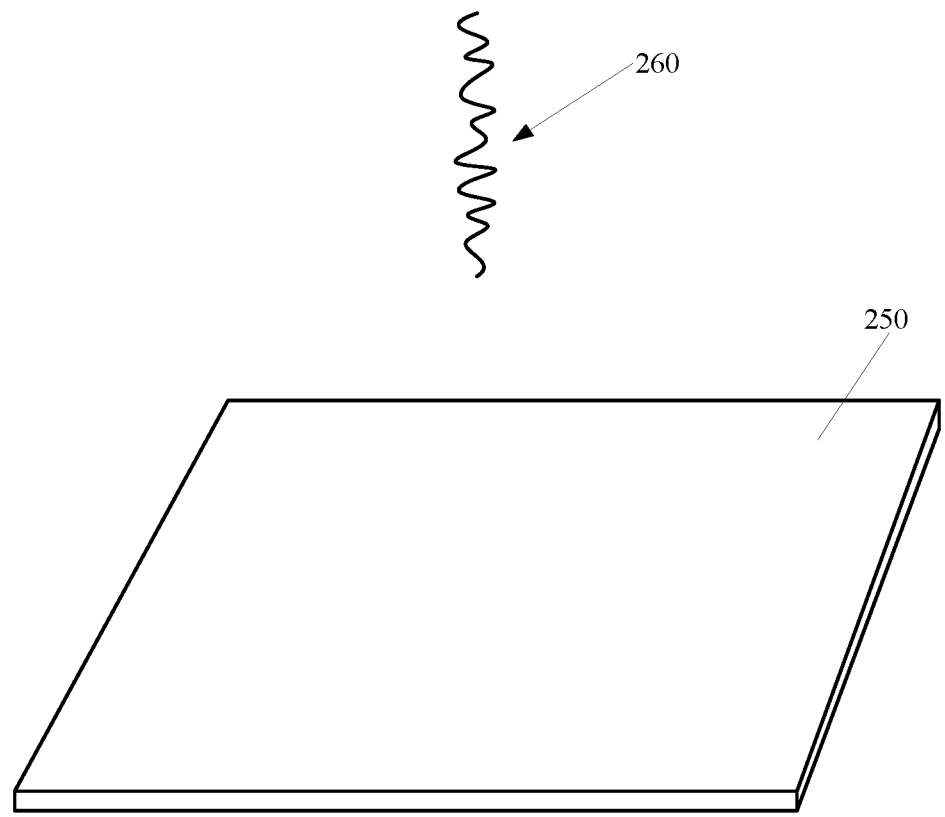

Referring to FIG. 6, a support plate 250 and an elastic support member 260 are provided.

The supporting plate 250 may include metal or a plastic tempered material.

A size of the support plate 250 may be greater than a size of the opening 241.

In some embodiments, when the edge of the opening 241 is rectangular, a surface of the support plate 250 is rectangular. The size of the support plate 250 being greater than the size of the opening 241 means that length of the support plate 250 is greater than length of the opening 241, and width of the support plate 250 is greater than width of the opening 241.

In some embodiments, the elastic support member 260 is a spring. In some embodiments, the elastic support member may be an elastic slice, an elastic foam or a damper.

When the elastic support member is an elastic foam, the elastic support member applies pressure to the optical fingerprint sensor module in a balanced manner, so as to avoid a crush damage to the optical fingerprint sensor module.

When elastic modulus of the elastic foam is within a range from 10 MPa to 1000 MPa, elasticity of the elastic foam is suitable, which is beneficial to a relative change of a distance between the support plate and the optical fingerprint sensor module, effectively prevents a lateral movement of the optical fingerprint sensor module relative to the support plate, and a damage to the optical fingerprint sensor 201 or even to the self-luminous display panel 220 is avoided.

Figure 7:
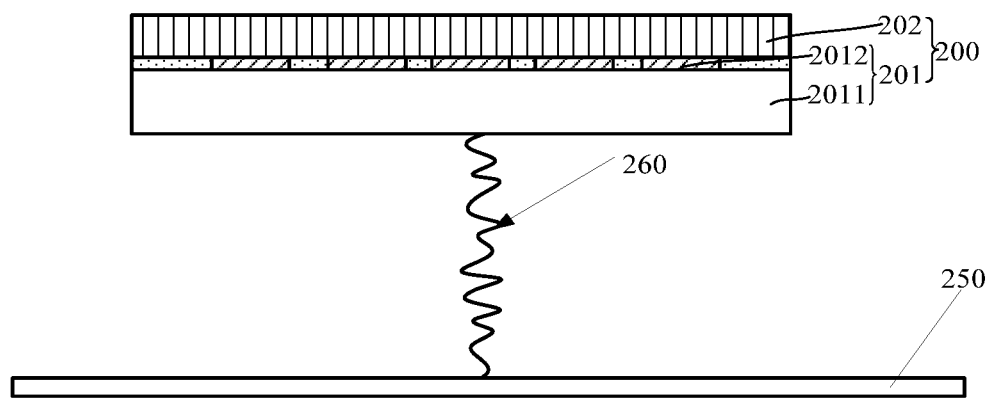

Referring to FIG. 7, the elastic support member 260 is disposed between the optical fingerprint sensor module 200 and the support plate 250, and the elastic support member 260 is fixedly connected to the optical fingerprint sensor module 200 and the support plate 250, respectively.

The elastic support member 260 may be fixedly connected to the optical fingerprint sensor module 200 by gluing or welding, and the elastic support member 260 may be fixedly connected to the support plate 250 by gluing or welding.

In some embodiments, the elastic support member 260 is a spring, and the spring has a first connection terminal and a second connection terminal opposite to each other in a compression direction of the spring. The first connection terminal is fixedly connected to the optical fingerprint sensor module 200, and the second connection terminal is fixedly connected to the support plate 250.

In some embodiments, the first connection terminal is fixedly connected to the sensor non-opaque substrate 2011. The collimator 202 and the elastic support member 260 are disposed on two sides of the optical fingerprint sensor 201, respectively.

Figure 8:
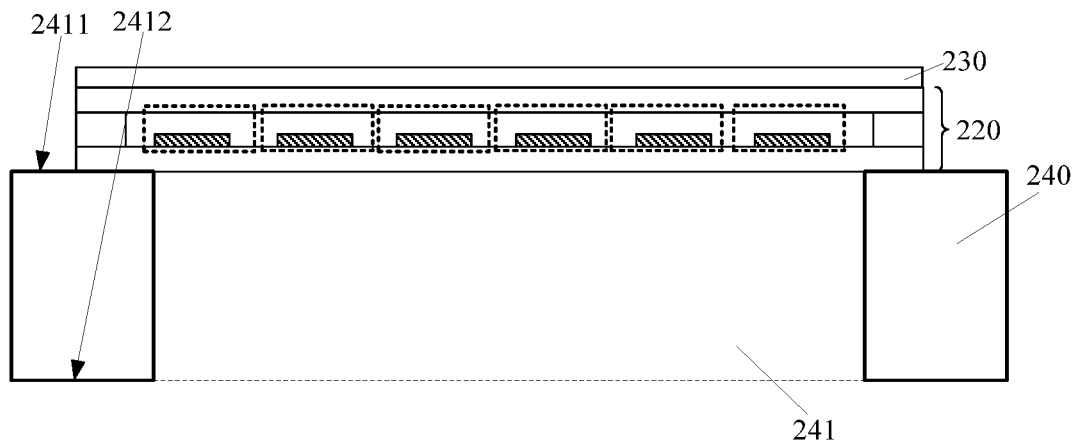

Referring to FIG. 8, the self-luminous display panel 220 and the support frame structure 240 are fixedly connected, and the self-luminous display panel 220 faces the opening 241.

In some embodiments, the self-luminous display panel 220 is fixed to the first frame connection surface 2411, and a display surface of the self-luminous display panel 220 faces away from the first frame connection surface 2411.

The self-luminous display panel 220 may be fixedly connected to the first frame connection surface 2411 by using thermosetting adhesive or double-sided adhesive.

In some embodiments, the method further includes: providing a cover layer 230; and adhering the self-luminous display panel 220 to the cover layer 230 prior to fixedly connecting the self-luminous display panel 220 to the support frame structure 240. After the self-luminous display panel 220 and the support frame structure 240 are fixedly connected, the cover layer 230 and the support frame structure 240 are disposed on two sides of the self-luminous display panel 220, respectively.

The cover layer 230 protects the self-luminous display panel 220.

The cover layer 230 may include a glass cover.

Figure 9:
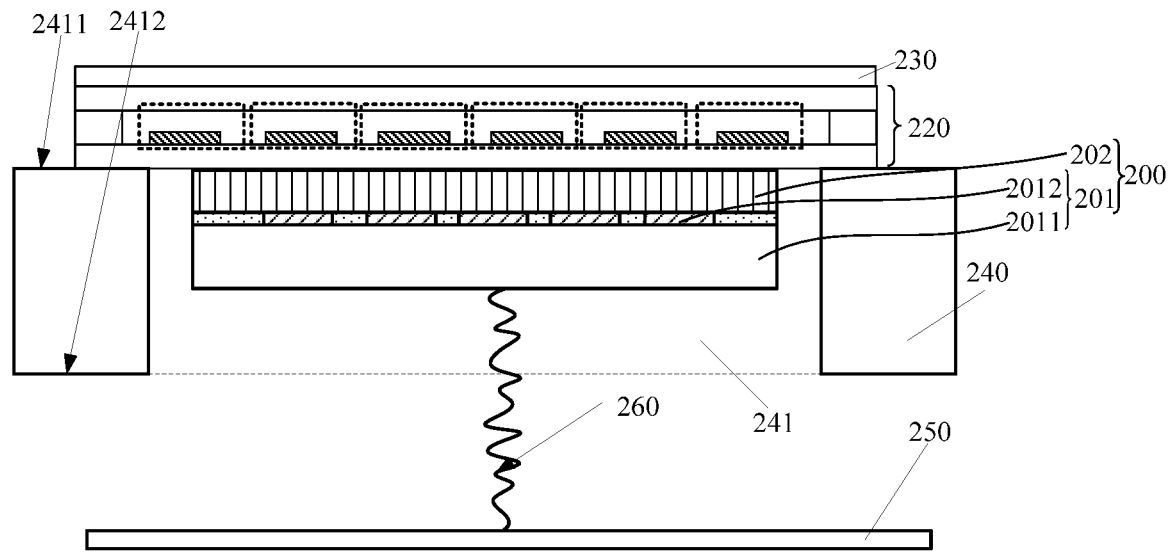

Referring to FIG. 9, after the self-luminous display panel 220 and the support frame structure 240 are fixedly connected, and the elastic support member 260 is fixedly connected to the optical fingerprint sensor module 200 and the support plate 250, respectively, the optical fingerprint sensor module 200 is disposed in the opening 241, the optical fingerprint sensor module 200 is disposed between the self-luminous display panel 220 and the support plate 250, and the support plate 250 further faces the support frame structure 240.

In some embodiments, the supporting plate 250 faces the second frame connection surface 2412.

Figure 10:
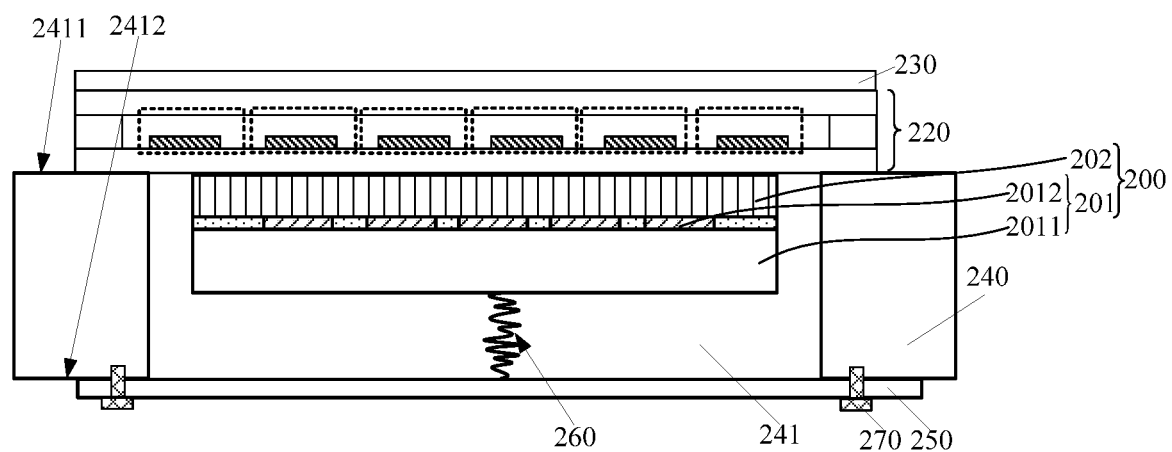

Referring to FIG. 10, following the optical fingerprint sensor module 200 is disposed in the opening 241, the elastic support member 260 is compressed, and the support plate 250 is fixedly connected to the support frame structure 240.

In some embodiments, the support plate 250 is fixedly connected to the second frame connection surface 2412.

In some embodiments, the optical fingerprint sensor module 200 is disposed in the opening 241, to make the optical fingerprint sensor module 200 contact with the self-luminous display panel 220. The elastic support member 260 is compressed, and the support plate 250 is fixedly connected to the support frame structure 240, to make the optical fingerprint sensor module 200 and the self-luminous display panel 220 squeeze each other.

In some embodiments, the support plate 250 and the support frame structure 240 are fixedly connected using a fastener 270. The fastener 270 penetrates through the support plate 250 and a portion of the support frame structure 240. The fastener 270 may include a bolt.

In some embodiments, the optical fingerprint sensor module 200 and the self-luminous display panel 220 are separable.

In some embodiments, as the optical fingerprint sensor module 200 and the self-luminous display panel 220 are separable, no sticking is required during an assembly process which is simple and convenient. Further, if the optical fingerprint sensor module 200 or the self-luminous display panel 220 is damaged, it is prone to separate the optical fingerprint sensor module 200 from the self-luminous display panel 220. As a result, the optical fingerprint sensor module 200 and the self-luminous display panel 220 may be reused, and cost may be reduced.

Accordingly, an optical fingerprint sensor apparatus formed by using the above assembling method is provided. Referring to FIG. 10, the optical fingerprint sensor apparatus includes: a support frame structure 240 having an opening 241 therein, the opening 241 penetrating through the support frame structure 240; an optical fingerprint sensor module 200 disposed in the opening 241; a support plate 250 disposed below the optical fingerprint sensor module 200 and at the bottom of the support frame structure 240, wherein the support plate 250 is fixedly connected to the bottom of the support frame structure 240; an elastic support member 260 disposed between the optical fingerprint sensor module 200 and the support plate 250, wherein the elastic support member 260 is fixedly connected to the optical fingerprint sensor module 200 and the support plate 250, respectively; and a self-luminous display panel 220 disposed on the optical fingerprint sensor module 200 and the support frame structure 240, wherein the self-luminous display panel 220 and the support frame structure 240 are fixedly connected.

In some embodiments, the optical fingerprint sensor module 200 includes an optical fingerprint sensor 201 and a collimator 202 disposed on the optical fingerprint sensor 201, wherein the collimator 202 is adhered to the optical fingerprint sensor 201, and is disposed between the optical fingerprint sensor 201 and the self-luminous display panel 220.

Detailed structures of the optical fingerprint sensor 201 and the collimator 202 can be found in the descriptions of the above embodiments, and are not described in detail here.

In some embodiments, the optical fingerprint sensor module may be an optical fingerprint sensor manufactured based on a CMOS process using a single crystal silicon as a substrate.

Detailed structures of the self-luminous display panel 220 can be found in the descriptions of the above embodiments, and are not described in detail here.

The support frame structure 240 has a first frame connection surface 2411 and a second frame connection surface 2412 opposite to each other. The opening 241 penetrates through the support frame structure 240 in a direction from the first frame connection surface 2411 to the second frame connection surface 2412.

A shape of the support frame structure 240 can be found in the descriptions of the above embodiments, and are not described in detail here.

A material and a size of the support plate 250 can be found in the descriptions of the above embodiments, and are not described in detail here.

The elastic support member 260 is disposed between the optical fingerprint sensor module 200 and the support plate 250. A first connection terminal of the elastic support member 260 is fixedly connected to the bottom of the optical fingerprint sensor module 200, and the second connection terminal of the elastic support member 260 is fixedly connected to the support plate 250.

In some embodiments, the elastic support member 260 is a spring, wherein the spring has a first connection terminal and a second connection terminal opposite to each other in a compression direction of the spring. The first connection terminal is fixedly connected to the bottom of the optical fingerprint sensor module 200, and the second connection terminal is fixedly connected to the support plate 250.

In some embodiments, the first connection terminal is fixedly connected to the sensor non-opaque substrate 2011. The collimator 202 and the elastic support member 260 are disposed on two sides of the optical fingerprint sensor 201, respectively.

In some embodiments, the elastic support member may be an elastic slice, an elastic foam or a damper.

When the elastic support member is an elastic foam, the elastic support member applies pressure to the optical fingerprint sensor module in a balanced manner, so as to avoid a crush damage to the optical fingerprint sensor module.

When elastic modulus of the elastic foam is within a range from 10 MPa to 1000 MPa, elasticity of the elastic foam is suitable, which is beneficial to a relative change of a distance between the support plate and the optical fingerprint sensor module, effectively prevents a lateral movement of the optical fingerprint sensor module relative to the support plate, and a damage to the optical fingerprint sensor 201 or even to the self-luminous display panel 220 is avoided.

The self-luminous display panel 220 and the support frame structure 240 are fixedly connected. In some embodiments, the self-luminous display panel 220 is fixedly connected to the first frame connection surface 2411, and a display surface of the self-luminous display panel 220 faces away from the first frame connection surface 2411.

The support plate 250 is fixedly connected to the support frame structure 240. In some embodiments, the support plate 250 is fixedly connected to the second frame connection surface 2412.

In some embodiments, the optical fingerprint sensor apparatus further includes a fastener 270 penetrating through the support plate 250 and a portion of the support frame structure 240. The fastener 270 includes a bolt.

In some embodiments, the optical fingerprint sensor apparatus further includes a cover layer 230 on the self-luminous display panel 220. The cover layer 230 protects the self-luminous display panel 220. The cover layer 230 may include a glass cover.

The cover layer 230 and the support frame structure 240 are disposed on two sides of the self-luminous display panel 220, respectively.

In some embodiments, the optical fingerprint sensor module 200 is in contact with the self-luminous display panel 220.

In some embodiments, the optical fingerprint sensor module 200 is in contact with and separable from the self-luminous display panel 220. The optical fingerprint sensor module 200 and the self-luminous display panel 220 squeeze each other.

An embodiment of the present disclosure also provides another method for assembling an optical fingerprint sensor apparatus. Compared with the previous embodiment as shown in FIGS. 2 to 10, this embodiment has following differences. The optical fingerprint sensor module includes a frame region. The method for assembling the optical fingerprint sensor apparatus further includes: providing a buffer layer; prior to disposing the optical fingerprint sensor module in the opening, adhering the buffer layer to a surface of the frame region of the optical fingerprint sensor module; following fixedly connecting the elastic support member to the optical fingerprint sensor module and the support plate, respectively, the buffer layer and the elastic support member being disposed on two sides of the optical fingerprint sensor module; during disposing the optical fingerprint sensor module in the opening, disposing the buffer layer in the opening, wherein the buffer layer is in contact with the self-luminous display panel; and during compressing the elastic support member, compressing the buffer layer. Similarity between this embodiment and the previous embodiment is not described in detail here.

FIGS. 11 to 14 schematically illustrate structural diagrams of an optical fingerprint sensor apparatus during its assembling process according to an embodiment.

Steps in the embodiment are performed based on the steps as shown in FIGS. 2 to 8 in the previous embodiment.

Figure 11:
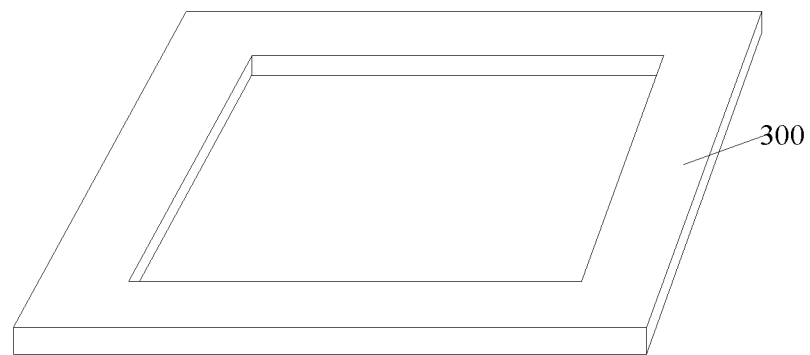
FIGS. 11 to 14 schematically illustrate structural diagrams of an optical fingerprint sensor apparatus during its assembling process according to another embodiment.

Referring to FIG. 11, a buffer layer 300 is provided.

The buffer layer 300 may include organic polymer, such as polystyrene, vinyl chloride, polyethylene terephthalate, polyethylene, polypropylene or polyester.

Elastic modulus of the buffer layer 300 is within a range from 100 MPa to 10000 MPa.

The buffer layer 300 has a certain function. The buffer layer 300 has certain elasticity and is not hard or sharp, so that the buffer layer 300 will not cause a damage, such as a scratch, to a lower surface of the self-luminous display panel 220 during an assembly process and a subsequent fingerprint identification process.

In the embodiment, the buffer layer 300 has a frame structure, so that there is a gap with certain size between an upper surface of the optical fingerprint sensor module 200 and the lower surface of the self-luminous display panel 200.

Figure 12:
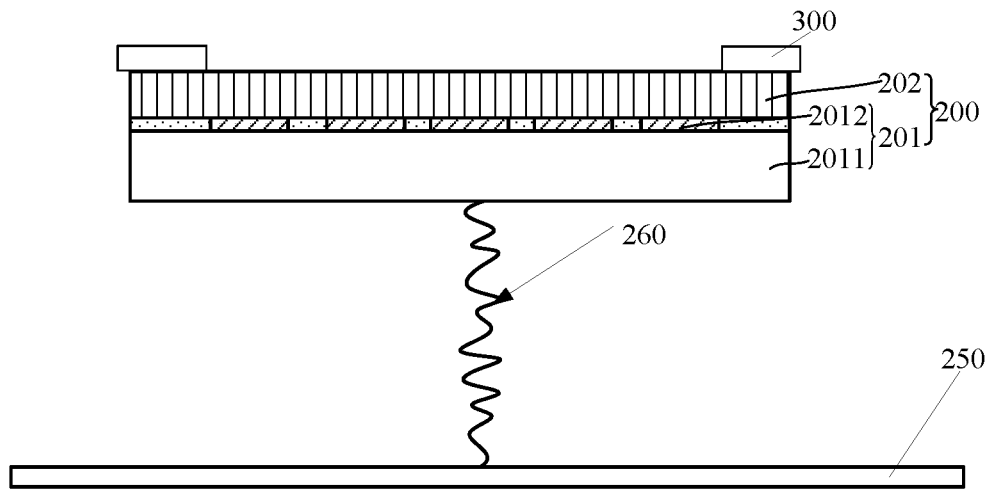

Referring to FIG. 12, the buffer layer 300 is adhered to a surface of the frame region of the optical fingerprint sensor module 200.

The optical fingerprint sensor module 200 includes an active region and a frame region disposed around the active region.

In some embodiments, after the elastic support member 260 is disposed between the optical fingerprint sensor module 200 and the support plate 250, and the elastic support member 260 is fixedly connected to the optical fingerprint sensor module 200 and the support plate 250, respectively, the buffer layer 300 is adhered to the surface of the frame region of the optical fingerprint sensor module 200.

The buffer layer 300 and the elastic support member 260 are disposed on two sides of the optical fingerprint sensor module 200, respectively.

In other embodiments, after the buffer layer is adhered to the surface of the frame region of the optical fingerprint sensor module, the elastic support member is disposed between the optical fingerprint sensor module and the support plate 250, and the elastic support member 260 is fixedly connected to the optical fingerprint sensor module and the support plate, respectively.

Figure 13:
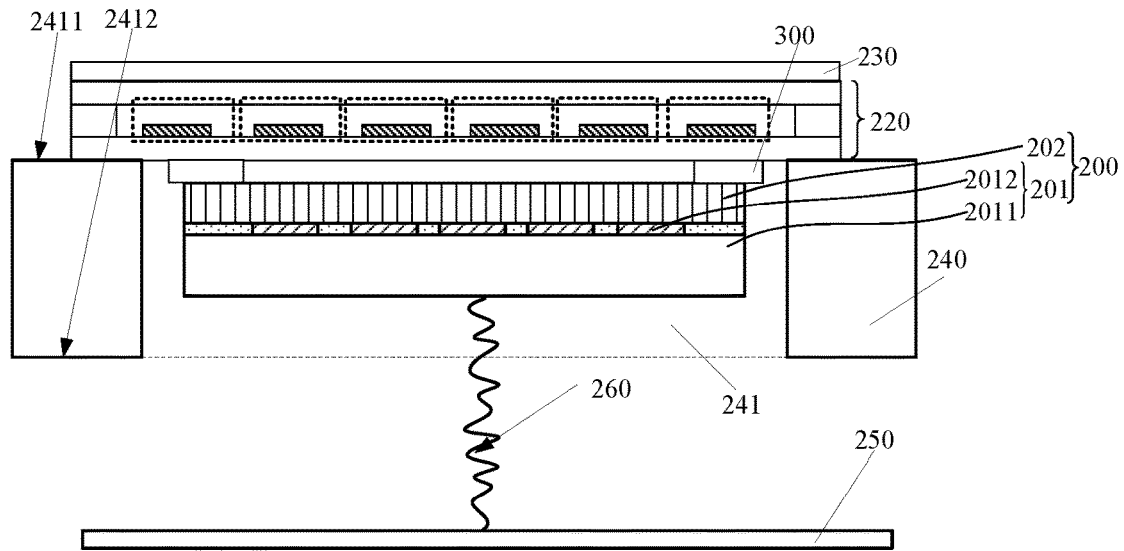

Referring to FIG. 13, after the self-luminous display panel 220 is fixedly connected to the support frame structure 240, and the elastic support member 260 is to fixedly connected to the optical fingerprint sensor module 200 and the support plate 250, respectively, the optical fingerprint sensor module 200 is disposed in the opening 241, to make the optical fingerprint sensor module 200 disposed between the self-luminous display panel 220 and the support plate 250. The support plate 250 further faces the support frame structure 240.

During a process of disposing the optical fingerprint sensor module 200 in the opening 241, the buffer layer 300 is disposed in the opening 241, and the buffer layer 300 is in contact with the self-luminous display panel 220.

Figure 14:
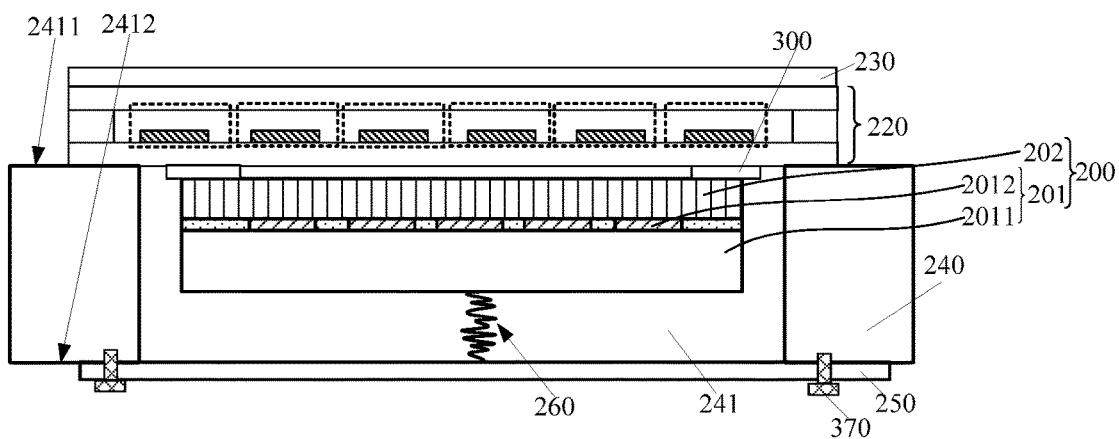

Referring to FIG. 14, after the optical fingerprint sensor module 200 is disposed in the opening 241, an elastic support member 260 is compressed, and the support plate 250 is fixedly connected to the support frame structure 240.

In some embodiments, the buffer layer 300 is compressed during a process of compressing the elastic support member 260. The buffer layer 300 is in contact with and separable from the self-luminous display panel 220.

Thickness of the buffer layer 300 in a compressed state is within a range from 0.05 mm to 1 mm, and a size of a gap between the self-luminous display panel 220 and the optical fingerprint sensor module 200 is within a range from 0.05 mm to 1 mm.

If the size of the gap between the self-luminous display panel 220 and the optical fingerprint sensor module 200 is greater than 1 mm, an optical signal will be deteriorated, and image sharpness will be deteriorated. If the size of the gap between the self-luminous display panel 220 and the optical fingerprint sensor module 200 is to less than 50 um, an uneven and thin gap layer is formed which may cause interference of light. It is prone to generate equal-thickness interference and further affect quality of fingerprint images.

In some embodiments, the support plate 250 and the support frame structure 240 are fixedly connected by using a fastener 370. The fastener 370 penetrates through the support plate 250 and a portion of the support frame structure 240. The fastener 370 may include a bolt.

Accordingly, an optical fingerprint sensor apparatus formed by using the above assembling method is provided. Referring to FIG. 14, the optical fingerprint sensor apparatus includes: a support frame structure 240 having an opening 241 therein, the opening 241 penetrating through the support frame structure 240; an optical fingerprint sensor module 200 disposed in the opening 241; a support plate 250 disposed below the optical fingerprint sensor module 200 and at the bottom of the support frame structure 240, wherein the support plate 250 is fixedly connected to the bottom of the support frame structure 240; an elastic support member 260 disposed between the optical fingerprint sensor module 200 and the support plate 250, wherein the elastic support member 260 is fixedly connected to the optical fingerprint sensor module 200 and the support plate 250, respectively; a self-luminous display panel 220 disposed on the optical fingerprint sensor module 200 and the support frame structure 240, wherein the self-luminous display panel 220 and the support frame structure 240 are fixedly connected; and a buffer layer 300 disposed between a frame region of the optical fingerprint sensor module 200 and the self-luminous display panel 220, wherein the buffer layer 300 is adhered to the frame region of the optical fingerprint sensor module 200, and is in contact with and separable from the self-luminous display panel 220.

The buffer layer 300 may include organic polymer, such as polystyrene, vinyl chloride, polyethylene terephthalate, polyethylene, polypropylene or polyester.

Elastic modulus of the buffer layer 300 is within a range from 100 MPa to 10000 MPa.

Thickness of the buffer layer 300 in a compressed state is within a range from 0.05 mm to 1 mm, and a size of a gap between the self-luminous display panel 220 and the optical fingerprint sensor module 200 is within a range from 0.05 mm to 1 mm.

In some embodiments, width of a frame of the buffer layer 300 is within a range from 0.5 mm to 1 mm.

Existing frame-shaped double-sided adhesive layer for adhering an optical fingerprint sensor module to a self-luminous display panel requires a relatively large area to ensure good adhesion properties of the optical fingerprint sensor module and the self-luminous display panel. Generally, width of a frame of the frame-shaped double-sided adhesive layer is greater than 1 mm and less than 2 mm.

In embodiments of the present disclosure, the buffer layer 300 merely needs to provide a buffer effect without an adhering function. Therefore, the buffer layer 300 may be designed to have a smaller size. Width of the frame of the buffer layer 300 is within a range from 0.5 mm to 1 mm. As the width of the frame of the buffer layer 300 is small, the frame region of the optical fingerprint sensor module 200 may be designed with a smaller area. In this way, an area of the entire optical fingerprint sensor module 200 becomes smaller, which improves integration of the optical fingerprint sensor module 200.

Structures in the optical fingerprint sensor apparatus provided in the embodiment as shown in FIGS. 11 to 14 same as those in the previous embodiment as shown in FIGS. 2 to 10 are not described in detail here.

Although the present disclosure has been disclosed above with reference to preferred embodiments thereof, it should be understood that the disclosure is presented by way of example only, and not limitation. Those skilled in the art can modify and vary the embodiments without departing from the spirit and scope of the present disclosure.

What is claimed is:

1. An optical fingerprint sensor apparatus, comprising:
   a support frame structure having an opening therein, the opening penetrating through the support frame structure;
   an optical fingerprint sensor module disposed in the opening;
   a support plate disposed below the optical fingerprint sensor module and at the bottom of the support frame structure, wherein the support plate is fixedly connected to the bottom of the support frame structure;
   an elastic support member disposed between the optical fingerprint sensor module and the support plate, wherein the elastic support member is fixedly connected to the optical fingerprint sensor module and the support plate, respectively; and
   a self-luminous display panel disposed on the optical fingerprint sensor module and the support frame structure, wherein the self-luminous display panel and the support frame structure are fixedly connected.

2. The optical fingerprint sensor apparatus according to claim 1, wherein the optical fingerprint sensor module is in contact with and separable from the self- luminous display panel.

3. The optical fingerprint sensor apparatus according to claim 1, wherein the optical fingerprint sensor module comprises a frame region, and the optical fingerprint sensor apparatus further comprises a buffer layer disposed between the frame region of the optical fingerprint sensor module and the self-luminous display panel, wherein the buffer layer is adhered to the frame region of the optical fingerprint sensor module, and is in contact with and separable from the self-luminous display panel.

4. The optical fingerprint sensor apparatus according to claim 3, wherein the buffer layer comprises organic polymer.

5. The optical fingerprint sensor apparatus according to claim 3, wherein elastic modulus of the buffer layer is within a range from 100 MPa to 10000 MPa.

6. The optical fingerprint sensor apparatus according to claim 3, wherein thickness of the buffer layer in a compressed state is within a range from 0.05 mm to 1 mm, and a size of a gap between the self-luminous display panel and the optical fingerprint sensor module is within a range from 0.05 mm to 1 mm.

7. The optical fingerprint sensor apparatus according to claim 1, wherein the elastic support member is a spring, wherein the spring has a first connection terminal and a second connection terminal opposite to each other in a compression direction of the spring, the first connection terminal is fixedly connected to the bottom of the optical fingerprint sensor module, and the second connection terminal is fixedly connected to the support plate.

8. The optical fingerprint sensor apparatus according to claim 1, wherein the elastic support member is an elastic foam.

9. The optical fingerprint sensor apparatus according to claim 8, wherein elastic modulus of the elastic foam is within a range from 10 MPa to 10000 MPa.

10. The optical fingerprint sensor apparatus according to claim 1, wherein the elastic support member is an elastic slice or a damper.

11. The optical fingerprint sensor apparatus according to claim 1, further comprising a fastener penetrating through the support plate and a portion of the support frame structure.

12. The optical fingerprint sensor apparatus according to claim 1, wherein the optical fingerprint sensor module comprises an optical fingerprint sensor and a collimator disposed on the optical fingerprint sensor, wherein the collimator is adhered to the optical fingerprint sensor, and is disposed between the optical fingerprint sensor and the self-luminous display panel.

13. The optical fingerprint sensor apparatus according to claim 1, further comprising a cover layer on the self-luminous display panel.

14. A method for assembling an optical fingerprint sensor apparatus, comprising:
    providing an optical fingerprint sensor module, a self-luminous display panel, a support plate, an elastic support member and a support frame structure, wherein the support frame structure has an opening therein which penetrates through the support frame structure;
    disposing the elastic support member between the optical fingerprint sensor module and the support plate, and fixedly connecting the elastic support member to the optical fingerprint sensor module and the support plate, respectively;
    fixedly connecting the self-luminous display panel to the support frame structure, wherein the self-luminous display panel faces the opening;
    following fixedly connecting the elastic support member to the optical fingerprint sensor module and the support plate, respectively and fixedly connecting the self-luminous display panel to the support frame structure, disposing the optical fingerprint sensor module in the opening, to make the optical fingerprint sensor module disposed between the self-luminous display panel and the support plate, wherein the support plate faces the support frame structure; and
    following disposing the optical fingerprint sensor module in the opening, compressing the elastic support member, and fixedly connecting the support plate to the support frame structure.

15. The method according to claim 14, wherein the optical fingerprint sensor module is disposed in the opening, to make the optical fingerprint sensor module contact with the self-luminous display panel, and the elastic support member is compressed and the support plate is fixedly connected to the support frame structure, to make the optical fingerprint sensor module and the self-luminous display panel squeeze each other.

16. The method according to claim 14, wherein the optical fingerprint sensor module comprises a frame region, and the method further comprises:
    providing a buffer layer;
    prior to disposing the optical fingerprint sensor module in the opening, adhering the buffer layer to a surface of the frame region of the optical fingerprint sensor module;
    following fixedly connecting the elastic support member to the optical fingerprint sensor module and the support plate, respectively, the buffer layer and the elastic support member being disposed on two sides of the optical fingerprint sensor module;
    during disposing the optical fingerprint sensor module in the opening, disposing the buffer layer in the opening, wherein the buffer layer is in contact with the self-luminous display panel; and
    during compressing the elastic support member, compressing the buffer layer.

17. The method according to claim 16, wherein the buffer layer comprises organic polymer, and elastic modulus of the buffer layer is within a range from 100 MPa to 10000 MPa.

18. The method according to claim 16, wherein thickness of the buffer layer in a compressed state is within a range from 0.05 mm to 1 mm, and a size of a gap between the self-luminous display panel and the optical fingerprint sensor module is within a range from 0.05 mm to 1 mm.

19. The method according to claim 14, wherein the support plate is fixedly connected to the support frame structure with a fastener.

20. The method according to claim 14, further comprising:
    providing a cover layer;
    prior to fixedly connecting the self-luminous display panel to the support frame structure, adhering the self-luminous display panel to the cover layer,
    wherein after the self-luminous display panel is fixedly connected to the support frame structure, the cover layer and the support frame structure are disposed on two sides of the self-luminous display panel.

* * * * *